(12) United States Patent
VanBlon et al.

(10) Patent No.: US 11,340,715 B2
(45) Date of Patent: May 24, 2022

(54) WEARABLE ACCESSORY DEVICE CHARGING

(71) Applicant: Lenovo (Singapore) Pte. Ltd., Singapore (SG)

(72) Inventors: Russell Speight VanBlon, Raleigh, NC (US); Nathan J. Peterson, Oxford, NC (US); Mark Patrick Delaney, Raleigh, NC (US); John Carl Mese, Cary, NC (US); Arnold S. Weksler, Raleigh, NC (US)

(73) Assignee: Lenovo (Singapore) Pte. Ltd., Singapore (SG)

( * ) Notice: Subject to any disclaimer, the term of this patent is extended or adjusted under 35 U.S.C. 154(b) by 226 days.

(21) Appl. No.: 16/687,242

(22) Filed: Nov. 18, 2019

(65) Prior Publication Data

US 2021/0149503 A1 May 20, 2021

(51) Int. Cl.
*G06F 3/0354* (2013.01)
*H02J 50/10* (2016.01)
*G06F 3/039* (2013.01)
*H02J 7/00* (2006.01)

(52) U.S. Cl.
CPC ........ *G06F 3/03543* (2013.01); *G06F 3/0395* (2013.01); *H02J 7/0042* (2013.01); *H02J 50/10* (2016.02); *G06F 2203/0332* (2013.01)

(58) Field of Classification Search
CPC .............. G06F 3/03543; G06F 3/0395; G06F 2300/0332; H02J 50/10; H02J 7/0042
USPC ........................................................ 320/108
See application file for complete search history.

(56) References Cited

U.S. PATENT DOCUMENTS

| | | | | |
|---|---|---|---|---|
| 2010/0109445 A1* | 5/2010 | Kurs | ..................... | B60L 53/122 307/104 |
| 2015/0162767 A1* | 6/2015 | Oh | ......................... | G06F 1/1632 320/108 |
| 2015/0277559 A1* | 10/2015 | Vescovi | .................. | G06F 1/163 345/173 |
| 2017/0117742 A1* | 4/2017 | Nakhjiri | ................. | H02J 7/0044 |
| 2017/0127196 A1* | 5/2017 | Blum | ...................... | H02J 50/12 |
| 2018/0337557 A1* | 11/2018 | Chen | .................. | H02J 7/00045 |
| 2019/0305591 A1* | 10/2019 | Ng | .......................... | H02J 50/40 |
| 2021/0004083 A1* | 1/2021 | Joseph | .................... | G06F 3/039 |

FOREIGN PATENT DOCUMENTS

CN    209657272 U   * 11/2019
CN    210137198 U   *  3/2020

* cited by examiner

*Primary Examiner* — Mark Edwards
(74) *Attorney, Agent, or Firm* — Ference & Associates LLC

(57) ABSTRACT

One embodiment provides a method, including: detecting, at a wireless charger integrated into an electronic device, a connection of a wearable accessory device, wherein the wireless charger is positioned proximate to a probable user contact position; and transmitting, using the wireless charger and during a period when the connection is established, a charge to the wearable accessory device; wherein the wearable accessory device is worn by a user during the connection. Other aspects are described and claimed.

12 Claims, 6 Drawing Sheets

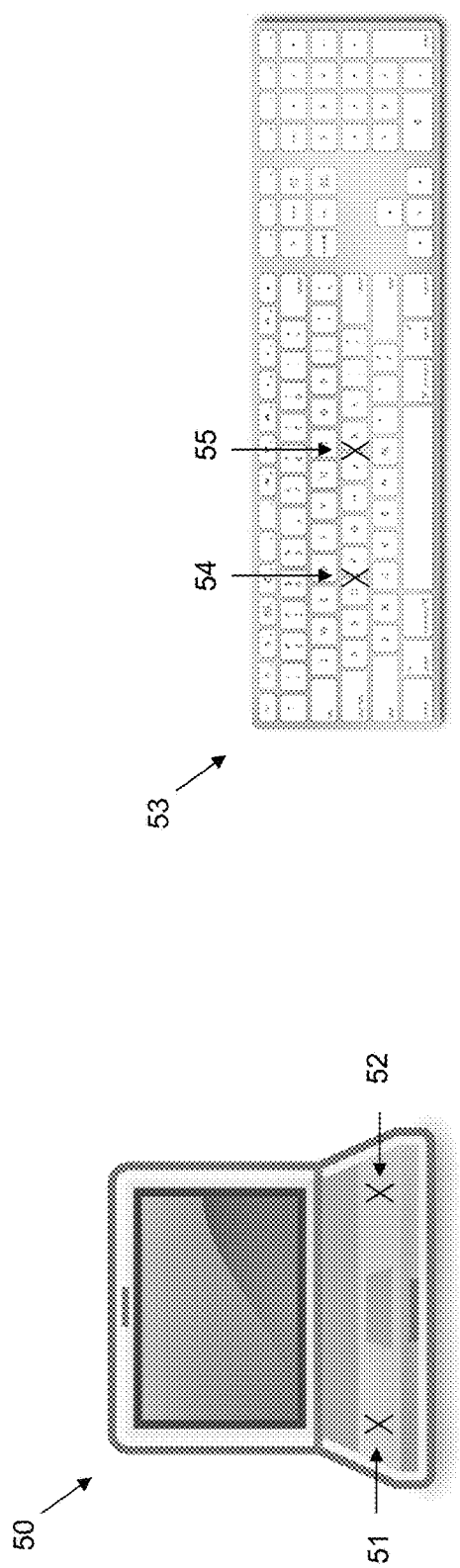
FIG. 5B
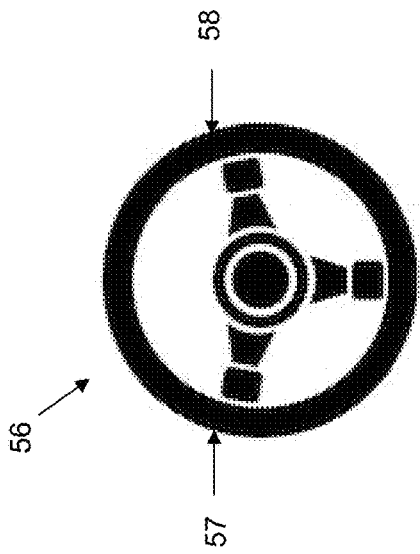
FIG. 5C
FIG. 5A

WEARABLE ACCESSORY DEVICE CHARGING

BACKGROUND

Wearable accessory devices, for example smart rings, smart watches, fitness trackers, and the like, have become prevalent in modern society. For example, fitness trackers and smart rings may be able to track a wearer's heart rate, record their daily steps or the number of daily calories burned, monitor their sleep cycle, and the like. As another example, many smart watches are capable of most or all of the foregoing and may also allow users to communicate with other individuals, access online content, listen to music, and the like.

BRIEF SUMMARY

In summary, one aspect provides a method, comprising: detecting, at a wireless charger integrated into an electronic device, a connection of a wearable accessory device, wherein the wireless charger is positioned proximate to a probable user contact position; and transmitting, using the wireless charger and during a period when the connection is established, a charge to the wearable accessory device; wherein the wearable accessory device is worn by a user during the connection.

Another aspect provides an electronic device, comprising: a wireless charger integrated into the electronic device, wherein the wireless charger is positioned proximate to a probable user contact position; a processor; a memory device that stores instructions executable by the processor to: detect a connection of a wearable accessory device to the wireless charger; and transmit, using the wireless charger and during a period the connection is established, a charge to the wearable accessory device; wherein the wearable accessory device is worn by a user during the connection.

A further aspect provides a method, comprising: detecting, using at least one sensor of an electronic device, user touch input at a position on a surface of the electronic device; determining, using a processor, whether the position corresponds to a wireless charging position; and transmitting, responsive to determining that the position corresponds to the wireless charging position and using a wireless charger positioned within the electronic device proximate to the wireless charging position, a charge to one or more proximate electronic devices.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

FIG. 5(A-C) illustrates example positions of at least two wireless chargers in an electronic device.

DETAILED DESCRIPTION

Figure 1:
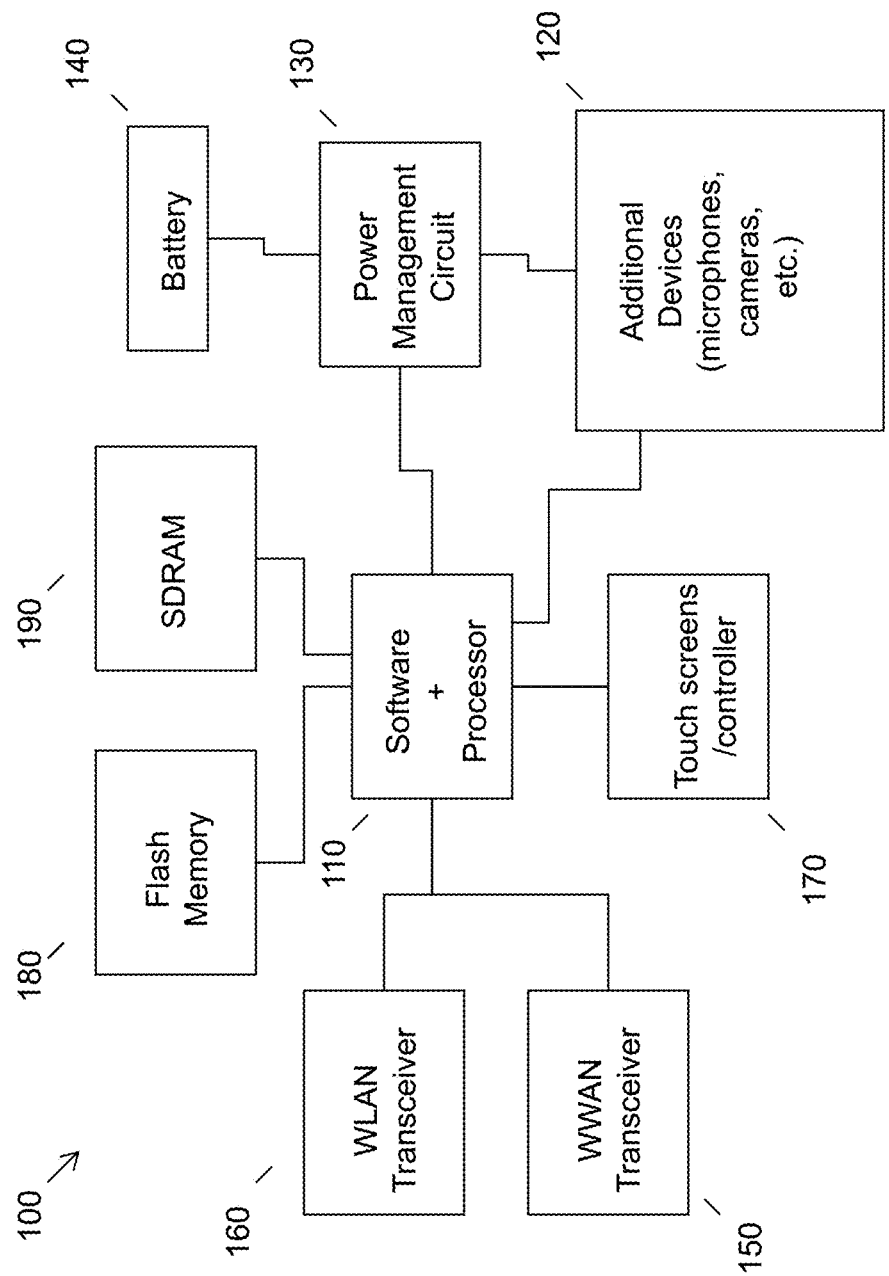
FIG. 1 illustrates an example of information handling device circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As with other electronic devices, wearable accessory devices ("wearables") need to eventually be charged. However, charging wearables can be quite burdensome and disruptive. More particularly, conventional charging methods require a user to remove the wearable and place it on a wireless charging pad, connect it to a charging cord, etc. While charging, the wearable is unable to track a user's biological data or be effectively utilized by the user to perform one or more other functions. A user may encounter similar issues in the reverse case where the wearable runs out of battery power while being worn.

Accordingly, an embodiment provides a method for wirelessly charging a wearable while the wearable is being worn by a user. In an embodiment, a connection to a wearable may be detected by a wireless charger of an electronic device. The electronic device may be virtually any object or device that a user's hands or wrists frequently interact with. For example, the electronic device may be one of a mouse, a laptop, a mouse pad, a steering wheel, etc. In an embodiment, the wireless charger may be integrated into a housing of the electronic device and may utilize a popular wireless charging standard such as Qi. In an embodiment, the connection between the wearable and the wireless charger may be established responsive to detecting that the wearable is within a predetermined proximate distance to the wireless charger. Subsequent to establishment of the connection, an embodiment may transmit a charge to the wearable. In this situation, a user may not need to remove the wearable from their person in order for it to charge. Such a method provides a more convenient and less disruptive way of charging a wearable.

The illustrated example embodiments will be best understood by reference to the figures. The following description is intended only by way of example, and simply illustrates certain example embodiments.

While various other circuits, circuitry or components may be utilized in information handling devices, with regard to smart phone and/or tablet circuitry 100, an example illustrated in FIG. 1 includes a system on a chip design found for example in tablet or other mobile computing platforms. Software and processor(s) are combined in a single chip 110. Processors comprise internal arithmetic units, registers, cache memory, busses, I/O ports, etc., as is well known in the art. Internal busses and the like depend on different vendors, but essentially all the peripheral devices (120) may attach to a single chip 110. The circuitry 100 combines the processor, memory control, and I/O controller hub all into a single chip 110. Also, systems 100 of this type do not typically use SATA or PCI or LPC. Common interfaces, for example, include SDIO and I2C.

There are power management chip(s) 130, e.g., a battery management unit, BMU, which manage power as supplied, for example, via a rechargeable battery 140, which may be recharged by a connection to a power source (not shown). In at least one design, a single chip, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additionally, devices 120 are commonly included, e.g., an image sensor such as a camera, audio capture device such as a microphone, etc. System 100 often includes one or more touch screens 170 for data input and display/rendering. System 100 also typically includes various memory devices, for example flash memory 180 and SDRAM 190.

Figure 2:
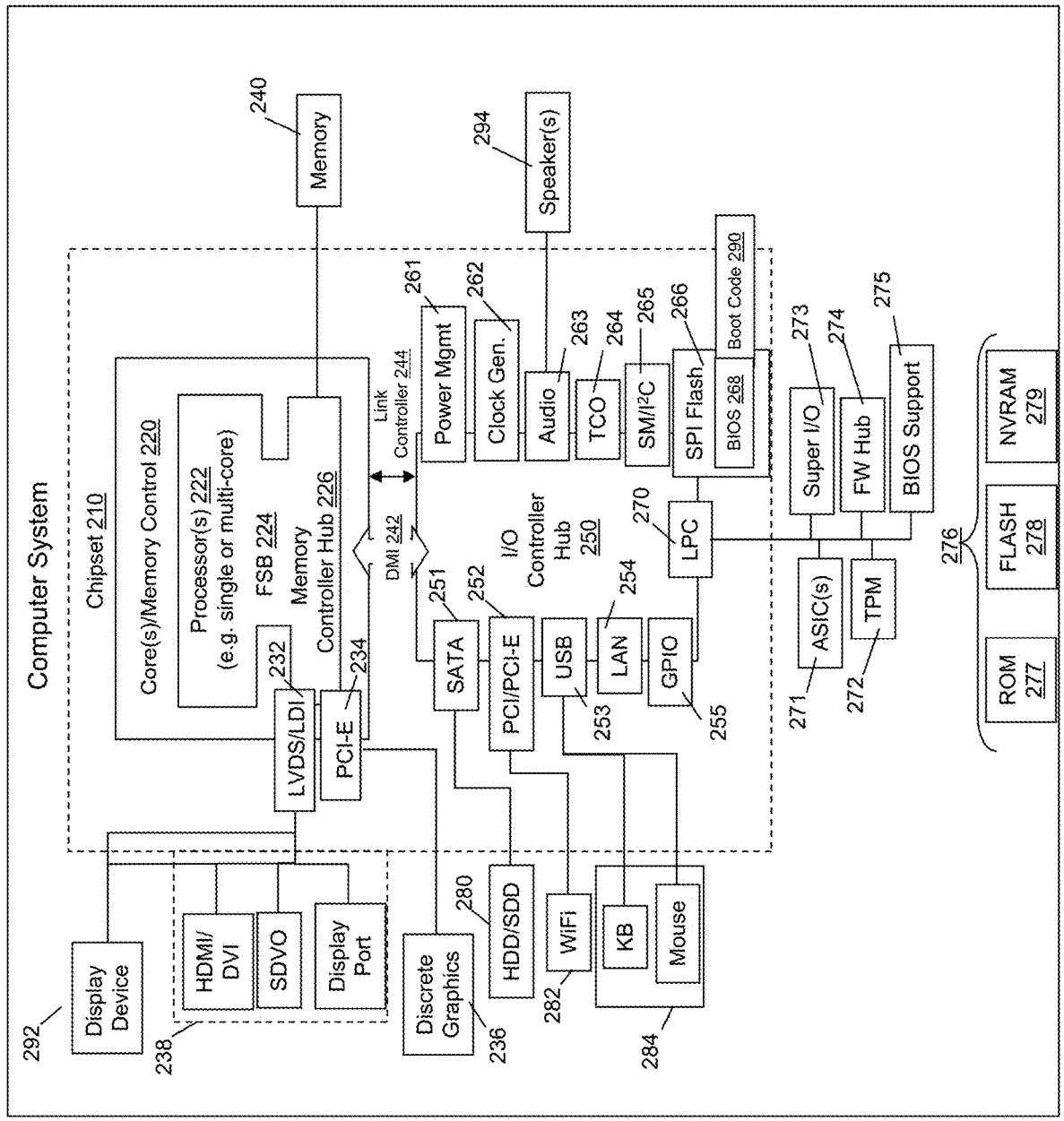
FIG. 2 illustrates another example of information handling device circuitry.

FIG. 2 depicts a block diagram of another example of information handling device circuits, circuitry or components. The example depicted in FIG. 2 may correspond to computing systems such as the THINKPAD series of personal computers sold by Lenovo (US) Inc. of Morrisville, N.C., or other devices. As is apparent from the description herein, embodiments may include other features or only some of the features of the example illustrated in FIG. 2.

The example of FIG. 2 includes a so-called chipset 210 (a group of integrated circuits, or chips, that work together, chipsets) with an architecture that may vary depending on manufacturer (for example, INTEL, AMD, ARM, etc.). INTEL is a registered trademark of Intel Corporation in the United States and other countries. AMD is a registered trademark of Advanced Micro Devices, Inc. in the United States and other countries. ARM is an unregistered trademark of ARM Holdings plc in the United States and other countries. The architecture of the chipset 210 includes a core and memory control group 220 and an I/O controller hub 250 that exchanges information (for example, data, signals, commands, etc.) via a direct management interface (DMI) 242 or a link controller 244. In FIG. 2, the DMI 242 is a chip-to-chip interface (sometimes referred to as being a link between a "northbridge" and a "southbridge"). The core and memory control group 220 include one or more processors 222 (for example, single or multi-core) and a memory controller hub 226 that exchange information via a front side bus (FSB) 224; noting that components of the group 220 may be integrated in a chip that supplants the conventional "northbridge" style architecture. One or more processors 222 comprise internal arithmetic units, registers, cache memory, busses, I/O ports, etc., as is well known in the art.

In FIG. 2, the memory controller hub 226 interfaces with memory 240 (for example, to provide support for a type of RAM that may be referred to as "system memory" or "memory"). The memory controller hub 226 further includes a low voltage differential signaling (LVDS) interface 232 for a display device 292 (for example, a CRT, a flat panel, touch screen, etc.). A block 238 includes some technologies that may be supported via the LVDS interface 232 (for example, serial digital video, HDMI/DVI, display port). The memory controller hub 226 also includes a PCI-express interface (PCI-E) 234 that may support discrete graphics 236.

In FIG. 2, the I/O hub controller 250 includes a SATA interface 251 (for example, for HDDs, SDDs, etc., 280), a PCI-E interface 252 (for example, for wireless connections 282), a USB interface 253 (for example, for devices 284 such as a digitizer, keyboard, mice, cameras, phones, microphones, storage, other connected devices, etc.), a network interface 254 (for example, LAN), a GPIO interface 255, a LPC interface 270 (for ASICs 271, a TPM 272, a super I/O 273, a firmware hub 274, BIOS support 275 as well as various types of memory 276 such as ROM 277, Flash 278, and NVRAM 279), a power management interface 261, a clock generator interface 262, an audio interface 263 (for example, for speakers 294), a TCO interface 264, a system management bus interface 265, and SPI Flash 266, which can include BIOS 268 and boot code 290. The I/O hub controller 250 may include gigabit Ethernet support.

The system, upon power on, may be configured to execute boot code 290 for the BIOS 268, as stored within the SPI Flash 266, and thereafter processes data under the control of one or more operating systems and application software (for example, stored in system memory 240). An operating system may be stored in any of a variety of locations and accessed, for example, according to instructions of the BIOS 268. As described herein, a device may include fewer or more features than shown in the system of FIG. 2.

Information handling device circuitry, as for example outlined in FIG. 1 or FIG. 2, may be used in devices capable of supporting an integrated wireless charger. For example, the circuitry outlined in FIG. 1 may be implemented in a laptop embodiment, whereas the circuitry outlined in FIG. 2 may be implemented in another computing source.

Figure 3:
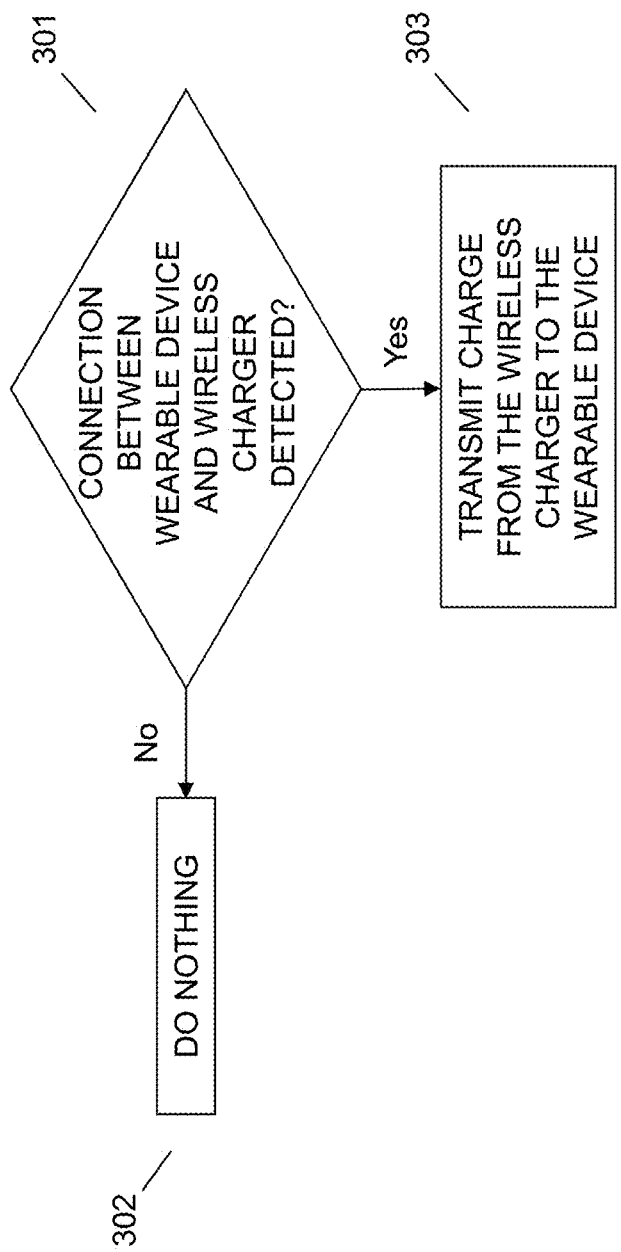
FIG. 3 illustrates an example method of wirelessly charging a wearable accessory device while the wearable accessory device is being worn by a user.

Referring now to FIG. 3, an embodiment may utilize a wireless charger integrated into an electronic device to charge a wearable accessory device while the wearable accessory device is worn by a user. At 301, an embodiment may detect a connection of a wearable accessory device ("wearable") to a wireless charger integrated into a housing of an electronic device. In an embodiment, the wireless charger may be capable of charging a battery source of another electronic device placed in close proximity to the wireless charger. For simplicity purposes, the remainder of this application will be described with reference to an inductive wireless charger that supports the Qi wireless charging standard (i.e., a Qi wireless charger). However, it is important to note that this designation is not intended to be limiting and other types of wireless chargers may also be utilized.

In the context of this application, an electronic device may refer to either: a conventional electronic device (e.g., laptop computer, a wireless mouse, a wireless keyboard, etc.) or another object capable of supporting one or more of the aforementioned wireless chargers within a housing of the object. For example, regarding the latter, a car steering wheel may not normally be considered an electronic device but, in this context of this application, may be considered as such because one or more wireless chargers may be positioned within and/or around the steering wheel.

In the context of this application, the wearable may correspond to virtually any type of wearable worn on, or close to, a user's hands or wrists that supports wireless Qi charging. For example, a wearable may correspond to a smart ring worn on a user's finger, a smart watch or fitness tracker worn on a user's wrist, and the like. In an embodiment, formation of a charging connection between the wearable and the wireless charger may be facilitated by placing the wearable within a predetermined proximate distance of the wireless charger (e.g., within 2-5 cm of the wireless charger, etc.).

Figure 4B:
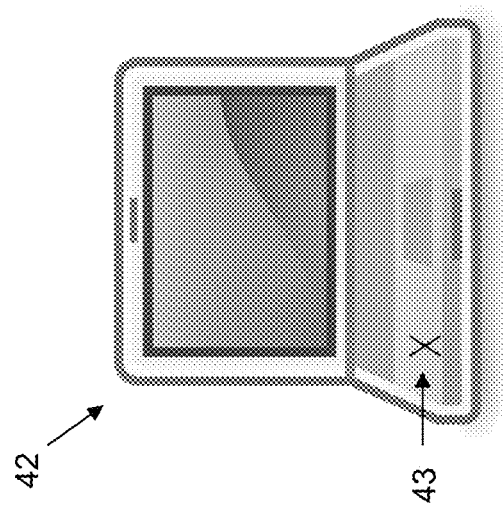
FIG. 4(A-B) illustrates example positions of a wireless charger in an electronic device.
Figure 4A:
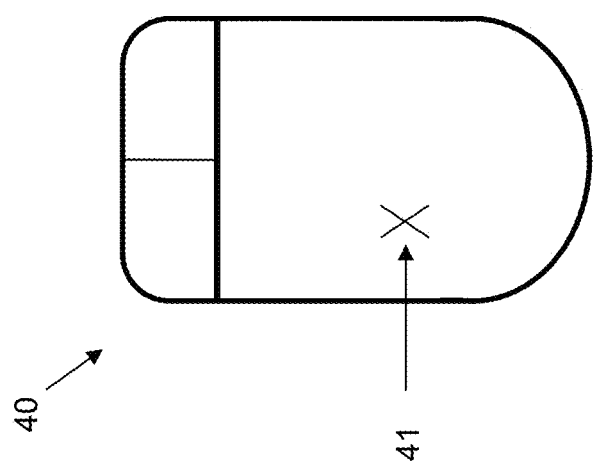

In an embodiment, the location of the wireless charger may vary widely and may be dependent on the electronic device that it is integrated in. More particularly, the location of the wireless charger may be a location that has a high likelihood of making proximate contact with a particular wearable worn on a user's hand or wrist. For example and with reference to FIG. 4A, in a wireless mouse 40, the wireless charger may be positioned at a substantially middle portion 41 of the wireless mouse to optimize proximate contact with a smart ring worn on a user's finger. As another example and with reference to FIG. 4B, in a laptop computer 42, a wireless charger may be positioned underneath a wrist rest portion 43 to optimize proximate contact with a smart watch or fitness tracker worn on the user's wrist.

In an embodiment, a singular electronic device may comprise two or more wireless chargers. Such an embodiment may ensure that a wearable may be able to form a connection with a wireless charger, regardless of which hand, finger, or wrist a wearable is being worn on. For example and with reference to FIG. 5A, a laptop computer 50 may contain two wireless chargers, with one located underneath each wrist rest area 51, 52 that bookends a track pad. Alternatively, in another example and with reference to FIG. 5B, a wireless keyboard 53 may contain two wireless chargers, with one located underneath the left side keys 54 and another located beneath the right side keys 55. In yet another example and with reference to FIG. 5C, a steering wheel 56 may contain a plurality of wireless chargers positioned underneath the common holding positions 57, 58 of the steering wheel.

Figure 6B:
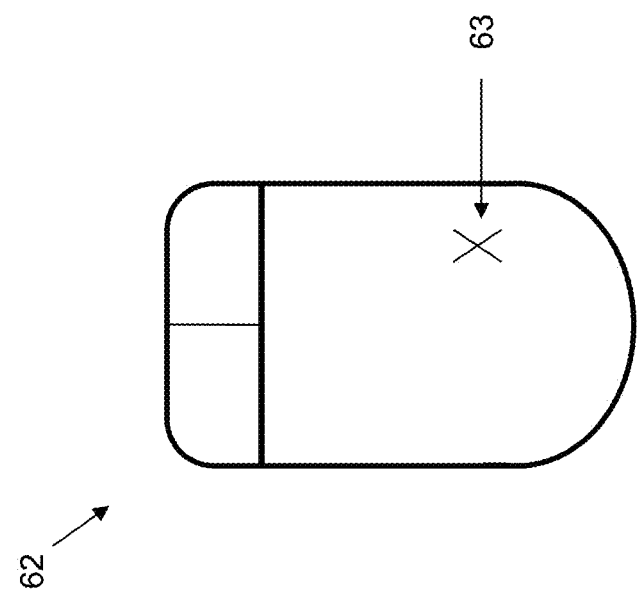
FIG. 6(A-B) illustrates a mouse containing an integrated wireless charger according to an embodiment.
Figure 6A:
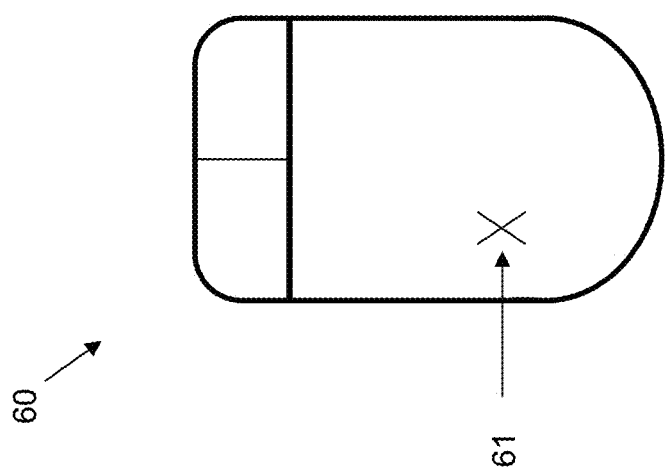

In an embodiment, an electronic device may contain a single wireless charger that may be movable to different locations within the electronic device. For example, with respect to a wireless mouse, the wireless charger may be positioned on a movable portion (e.g., a movable slider, etc.) that may be adjusted horizontally and/or vertically to adjust the position of the wireless charger within the wireless mouse. Such an embodiment may allow for variation in the optimal charge location. For example and with reference to FIG. 6A, if a user interacts with a wireless mouse 60 with their right hand and wears a smart ring on their right index finger, then an initial position of the wireless charger may be underneath a left-middle portion 61 of the mouse 60. If, however, a user were to move their smart ring to their right middle finger, or wore another smart ring on their right middle finger that they wanted to charge, the user could, for instance, remove a top housing of the mouse, slide the movable portion containing the wireless charger toward a right-middle portion 63 of the mouse 62, as indicated in FIG. 6B, and then replace the top-housing of the mouse. Thereafter, the wireless charger may be in an optimal position to charge the smart ring worn on the middle finger.

In an embodiment, the electronic device may comprise one or more magnetic portions. In an embodiment, the magnetic portion(s) may be located on a surface of the electronic device, above or proximate to the location where the wireless charger is located. In an embodiment, the magnetic portion(s) may serve to guide and secure the wearable to an optimal charging location on the surface of the electronic device.

If a connection is not established, at 301, an embodiment may, at 302, take no further action. Conversely, if a connection is established, at 301, an embodiment may, at 303, transmit a charge to the wearable from the wireless charger. In an embodiment, the charge may be transmitted while the wearable is being worn by the user. More particularly, as a user is interacting with the electronic device (e.g., moving the wireless mouse, typing on the wireless keyboard, manipulating the steering wheel, etc.) their wearable may charge.

In an embodiment, a notification may be provided to the user when their wearable is fully charged. The notification may be one or more of: a haptic notification (e.g., occurring at the wearable or at the electronic device, etc.), an audible notification (e.g., provided through one or more speakers associated with the wearable or with the electronic device, etc.), a visual notification (e.g., provided through a display screen associated with the wearable or with the electronic device, etc.), any combination of the foregoing, and the like.

In an alternative embodiment, the electronic device may comprise one or more sensors (e.g., camera sensors, touch sensors, etc.) that may be able to detect when a user has touched the electronic device. More particularly, these sensors may be able to detect a position, on the surface of the electronic device, where the user touch was detected. An embodiment may thereafter determine whether this position corresponds to a wireless charging position. In an embodiment, the wireless charging position may be a probable user contact position, as described above, and may also be a position where the detection of user touch influences a system of the electronic device to instruct an integrated wireless charger to begin transmitting a wireless charge. If another electronic device (e.g., a wearable, etc.) is proximate to the wireless charging position during this transmission, then they may receive the wireless charge to power a battery.

The various embodiments described herein thus represent a technical improvement to conventional methods for charging a wearable device. Using the techniques described herein, an embodiment may allow a user to continue wearing their wearable device while the device is being charged. In an embodiment, an electronic device that a user frequently interacts with (e.g., a laptop, a mouse, a keyboard, etc.) may comprise an integrated wireless charger (e.g., a wireless Qi charger, etc.). Responsive to establishing a connection with the user's wearable (e.g., by identifying that a user's wearable is in proximity to an electronic device, etc.) an embodiment may charge the wearable while the wearable is still being worn by the user. Such an embodiment negates the conventional need for the user to remove their wearable device while charging and may allow for more continuous data gathering, processing, and user utilization.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, a system, apparatus, or device (e.g., an electronic, magnetic, optical, electromagnetic, infrared, or semiconductor system, apparatus, or device) or any suitable combination of the foregoing. More specific examples of a storage device/medium include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:
   detecting, at a wireless charger integrated into a mouse, a connection of a wearable accessory device, wherein the wireless charger is disposed within a movable portion of the mouse movable between at least two positions for positioning proximate to a probable user contact position; and
   transmitting, using the wireless charger and during a period when the connection is established, a charge to the wearable accessory device;
   wherein the wearable accessory device is worn by a user during the connection.

2. The method of claim 1, wherein the wireless charger is an inductive charger utilizing the Qi standard.

3. The method of claim 1, wherein the mouse is a mouse pad.

4. The method of claim 1, further comprising providing a notification to a user responsive to identifying that the wearable accessory device is fully charged.

5. The method of claim 4, wherein the notification is selected from the group consisting of a haptic notification, an audible notification, and a visual notification.

6. The method of claim 1, wherein the probable user contact position corresponds to an optimal charging portion and wherein the mouse comprises a magnetic portion configured to secure the wearable accessory device to the optimal charging portion.

7. A mouse, comprising:
   a wireless charger integrated into the mouse, wherein the wireless charger is disposed within a movable portion of the mouse movable between at least two positions for positioning proximate to a probable user contact position;
   a processor;
   a memory device that stores instructions executable by the processor to:
   detect a connection of a wearable accessory device to the wireless charger; and
   transmit, using the wireless charger and during a period the connection is established, a charge to the wearable accessory device;
   wherein the wearable accessory device is worn by a user during the connection.

8. The mouse of claim 7, wherein the wireless charger is an inductive charger utilizing the Qi standard.

9. The mouse of claim 7, wherein the mouse is a mouse pad.

10. The mouse of claim 7, wherein the instructions are further executable by the processor to provide a notification to a user responsive to identifying that the wearable accessory device is fully charged.

11. The mouse of claim 7, wherein the probable user contact position corresponds to an optimal charging portion and wherein the mouse comprises a magnetic portion configured to secure the wearable device to the optimal charging portion.

12. A method, comprising:
- detecting, using at least one sensor of a mouse, an input from a user touch at a position on a surface of the mouse, wherein a wireless charger is disposed within a movable portion of the mouse movable between at least two positions for positioning proximate to a probable user contact position;
- determining, using a processor, whether the position corresponds to a wireless charging position; and
- transmitting, responsive to determining that the position corresponds to the wireless charging position and using the wireless charger positioned within the mouse proximate to the wireless charging position, a charge to one or more proximate electronic devices.

* * * * *